United States Patent [19]

Dewanckele et al.

[11] Patent Number: 5,198,333
[45] Date of Patent: Mar. 30, 1993

[54] PHOTOGRAPHIC MATERIALS CONTAINING ELECTRON ACCEPTING AGENTS

[75] Inventors: Jean-Marie O. Dewanckele, Drongen; Paul R. Callant, Edegem; Marc H. Van Bockstaele, Mortsel; Marc B. Graindourze, Overpelt, all of Belgium

[73] Assignee: Agfa-Gevaert, N.V., Mortsel, Belgium

[21] Appl. No.: 668,624

[22] Filed: Mar. 13, 1991

[30] Foreign Application Priority Data

Mar. 19, 1990 [EP] European Pat. Off. ........ 90200646.9

[51] Int. Cl.$^5$ .............................................. G03C 1/34
[52] U.S. Cl. .................................... 430/597; 430/264; 430/600; 430/603; 430/606; 430/611; 430/613; 430/614; 430/640
[58] Field of Search ................ 430/597, 600, 603, 606, 430/611, 613, 614, 940, 264, 567, 640

[56] References Cited

U.S. PATENT DOCUMENTS 4,495,274  1/1985  Yoshida ................................ 430/614
4,820,625  4/1989  Saeki et al. ........................... 430/597

FOREIGN PATENT DOCUMENTS 335319  10/1989  European Pat. Off. .
60-178445  9/1985  Japan .................................. 430/611

Primary Examiner—Charles L. Bowers, Jr.
Assistant Examiner—Janet C. Baxter
Attorney, Agent, or Firm—Breiner & Breiner

[57] ABSTRACT

A new class of electron-accepting compounds for photographic emulsions is disclosed represented by following general formula (I):

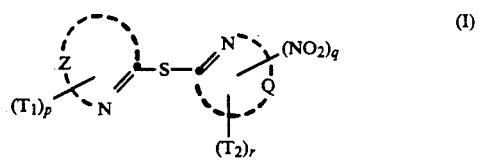

wherein:
each of Z and Q which may be the same or different represents the atoms necessary to complete an unsubstituted or substituted nitrogen-containing heterocyclic ring;
each of $T_1$ and $T_2$ which may be the same or different represents alkyl, cycloalkyl, alkoxy, aryl, aryloxy, halogen, cyano, hydroxy, carboxyl, sulfo, carbamoyl, acyl, acylamino, sulfamoyl, sulfonamido or a benzo-condensed ring, each of which can be further substituted or not;
q=1, 2 or 3, and p and r=0, 1 or 2.

In this formula the nitro containing heterocyclic nucleus is preferably nitropyridine or nitrothiazole.

In a preferred embodiment of the invention electron-accepting compounds are incorporated in negative or direct positive roomlight emulsions. In the latter case the emulsion layer preferably contains in addition a nitroindazole or nitrobenzimidazole derivative.

8 Claims, No Drawings

PHOTOGRAPHIC MATERIALS CONTAINING ELECTRON ACCEPTING AGENTS

BACKGROUND OF THE INVENTION

The present invention relates to photographic materials containing a new class of electron-accepting compounds.

Electron accepting agents are useful for both negative and direct positive working silver halide photographic materials. For negative working materials electron-accepting agents are usually called spectral desensitizers. They are able to lower the sensitivity of the material in the spectral range of their absorption. Of course, combinations of desensitizers with different spectral regions are possible.

Prior art concerning electron-accepting compounds suitable for use in negative working or direct positive emulsions, includes nitrostyryl and nitrobenzylidene dyes as described in U.S. Pat. No. 3,615,610, dihydropyrimidine compounds of the type disclosed in DE 2,237,036 and compounds of the type disclosed in U.S. Pat. No. 3,531,290. Other useful electron accepting compounds are cyanine and merocyanine dyes containing at least one nucleus, and preferably two nuclei with desensitizing substituents such as nitro groups, or dyes containing desensitizing basic nuclei as described in U.S. Pat. Nos. 2,930,644, 3,431,111, 3,492,123, 3,501,310, 3,501,311, 3,574,629, 3,579,345, 3,598,595, 3,592,653, and GB 1,192,384.

Electron accepting compounds belonging to the class of nitrophenylthioether derivatives are disclosed in U.S. Pat. No. 4,820,625.

In the sector of pre-press activity known as graphic and reprographic arts an intensive use is made of contact copying materials to reproduce screen dot images, line work and typesetting work. Both negative working photographic materials which produce negative-positive or positive-negative copies are used as well as so-called direct positive working materials giving rise to negative-negative or positive-positive reproductions.

In order to obtain exact copies with sharp dot and line edges, it is necessary to use fine-grained relatively insensitive photographic emulsions. The materials containing this type of emulsions are image-wise exposed in contact with the original in a graphic arts copying apparatus by means of high intensity radiation, preferably by light sources emitting a high content of near-ultraviolet light. Common light sources for this purpose are mercury vapour lamps, metal-halogen lamps, xenon tubes, pulsed xenon tubes and quartz-halogen sources.

The handling of ever increasing amounts of photographic materials of different kinds, the decentralisation of the distinct steps in the reproduction cycle etc, have created a demand for silver halide materials which can be handled under clear ambient light illumination. This demand has given rise to the development of so called "roomlight materials" which can be image-wise exposed, handled and processed without sensitometric changes in a reasonable time interval while being illuminated by common office fluorescent tubes and daylight penetrating through office windows. Prior art material which can be handled under roomlight conditions has been described in e.g. U.S. Pat. No. 2,219,667 and GB 1,330,044.

Silver halide emulsions contained in such roomlight materials should exhibit adequate sensitivity and other sensitometric characteristics for image-wise exposure while showing no photographic response under ambient light conditions. It is the task of the emulsion designer to establish the optimal compromise between these two conflicting characteristics.

For negative working roomlight applications the intrinsic sensitivity of silver halide is usually too high; lowering of the sensitivity is possible by incorporating internal electron traps being centers promoting the deposition of photolytic silver in the interior parts of the silver halide grains and/or by the addition of electron-accepting agents to the silver emulsion, as is the case in this application. The latter method shows the advantage that these spectral desensitizers usually induce a pronounced Low Intensity Reciprocity Failure (LIRF) which is one of the factors promoting excellent roomlight stability. This excellent roomlight stability further requires the use of emulsions mainly composed of chloride (at least 70%) the spectral sensitivity distribution of which is restricted to the near ultraviolet. Incorporation of too much bromide or iodide in the emulsion extends the spectral sensitivity distribution too much into the visible region (see F. Moser and R. K. Ahrenkiel in "The Theory of the Photographic Process", edited by Th. James and published by Macmillan Publ. Co., Inc., New York (1977), p. 39.). A spectral desensitizer when present should show a similar spectral absorption limited to the near ultraviolet in order to avoid extension of the sensitivity into the visible region.

Direct positive working roomlight emulsions can function according to different emulsion technology principles. They can contain internal traps due to the presence of phase boundaries in the so-called core-shell emulsion type. They can function according to internal electron trapping due to the building in of inorganic desensitizers, e.g. metal dopants, in the interior of the silver halide crystals. In these cases of internal trapping, the emulsion surface can be fogged or not; in the latter case usually a reducing agent is present in the photographic material or in its developing solution, e.g. a hydrazine derivative. Finally they can work according to the principles of external electron trapping in which case the emulsion surface is prefogged and an electron-accepting compound is adsorbed at it.

Relatively sensitive direct positive emulsions can be composed of AgBr or AgBrI; in this case however red safety light conditions as present in classical darkrooms are required. Rather insensitive direct positive AgBr(I) emulsions exist, suited for exposure by quartz-halogen sources, which can be handled under relative bright yellow light conditions. For roomlight direct positive applications however it is, like in the corresponding negative case, necessary to use emulsions with a high content of chloride in order to minimize the overlap between the intrinsic sensitivity and the roomlight spectrum. If the absorption of the external electron-accepting agent would extend to the visible region, as it is e.g. the case with the well known electron-accepting agent Pinakryptol Yellow (further indicated as Reference Compound R-1), this would lead under roomlight to the bleaching of the latent image created by the prefogging of the emulsion.

It is one of the purposes of the present invention to provide a new class of electron acceptors which do not show the disadvantage of inadequate spectral absorption.

SUMMARY OF THE INVENTION

It is an object of the present invention to provide a new class of electron-accepting agents for use in both negative and direct positive working silver halide photographic materials.

It is a further object of this invention to provide such electron acceptors which show an adequate spectral absorption which does not extend into the visible spectral region.

Other objects will become apparent from the description hereafter.

According to the present invention this new class of electron-accepting compounds can be described as thioethers containing two heterocyclic nitrogen comprising nuclei with general formula (I):

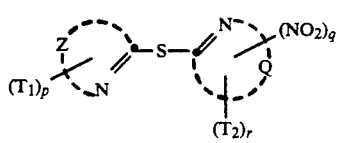

wherein:
each of Z and Q which may be the same or different represents the atoms necessary to complete a unsubstituted or substituted nitrogen-containing heterocyclic ring;
each of $T_1$ and $T_2$ which may be the same or different represents alkyl, cycloalkyl, alkoxy, aryl, aryloxy, halogen, cyano, hydroxy, carboxyl, sulfo, carbamoyl, acyl, acylamino, sulfamoyl, or sulfonamido;
q=1, 2 or 3, and p and r=0, 1 or 2.

In this formula the nitro containing heterocyclic nucleus is preferably nitropyridine or nitrothiazole.

Although some representatives of this general formula were known earlier e.g. from pharmaceutical research it is the first time that their use as active photographic ingredients is disclosed.

In a preferred embodiment of the present invention the newly disclosed electron-accepting compounds are present in photographic materials containing negative or direct positive roomlight emulsions. In the case of direct positive roomlight emulsions, the emulsion layer preferably further contains a nitroindazole or a nitrobenzimidazole derivative.

A detailed description of several embodiments of this invention is presented hereafter.

DETAILED DESCRIPTION OF THE INVENTION

In the general formula (I), specific examples of nitrogen containing heterocyclic rings include unsubstituted or substituted triazole, tetrazole, thiazole, thiadiazole, oxazole, oxadiazole, imidazole, indazole, pyridine, pyrimidine, quinoline, triazaindene, tetrazaindene, pentazaindene and so on.

As stated above some representatives according to the general formula are known from pharmaceutical research. So p,p'-dinitro-di-2-pyridyl-thioether is disclosed as antibacterial agent in Farmaco, Ed. Sci., 34(12), 1015-21. 3-nitropyridyl-pyrimidyl-thioether derivatives are mentioned in Ann. Pharm. Fr., 38(3), 267-70 for antimitotic activity. Other compounds according to the general formula of the invention are disclosed in J. Pharm. Belg., 32(6), 533-8, in J. Org. Chem., 41(21), 3395-9 and in Indian J. Chem., sect. B, 14B10, 756-8. However, it is the first time that their use as active photographic ingredients is disclosed.

Specific examples of useful compounds according to the present invention are presented below; however the invention should not be considered as restricted to the given examples:

Compound I-1

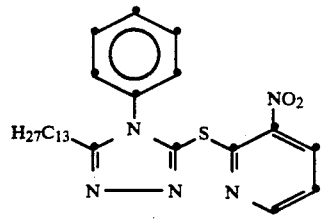

Compound I-2

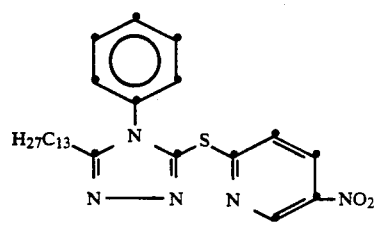

Compound I-3

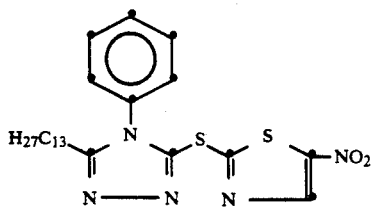

Compound I-4

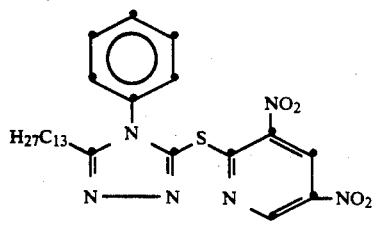

Compound I-5

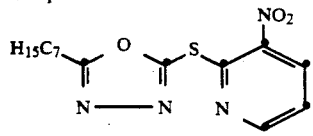

Compound I-6

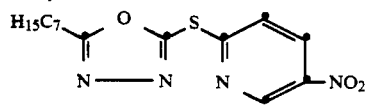

Compound I-7

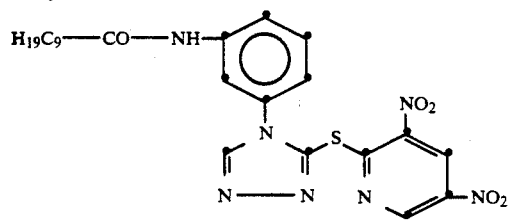

Compound I-8

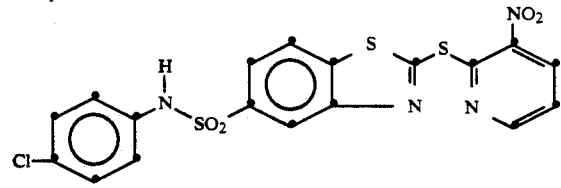

Reference Compound R-1: Pinakryptol Yellow

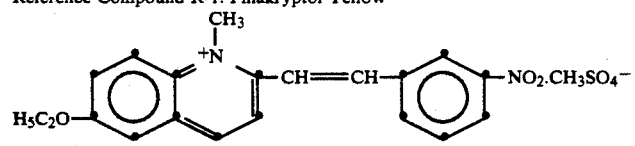

The electron-accepting compounds of the present invention are present in the light sensitive layer(s) of the photographic material and are adsorbed at the surface of the silver halide grains. The silver halide emulsion(s) can be present in a single layer or in a multi-layer pack, e.g. a double layer. Preferably the electron-accepting compounds are present in a concentration ranging from $10^{-5}$ mole to $10^{-1}$ mole per mole silver halide.

Beside the light sensitive emulsion layer(s) the photographic material can contain several non-light sensitive layers, e.g. a protective layer, one or more backing layers, and one or more intermediate layers which may contain filter or antihalation dyes that absorb scattering light and thus promote the image sharpness. Suitable light-absorbing dyes are described in e.g. U.S. Pat. Nos. 4,092,168, 4,311,787, DE 2,453,217, and GB 7,907,440.

One or more backing layers can be provided at the non-light sensitive side of the support. These layers which can serve as anti-curl layers can contain e.g. matting agents e.g. silica particles, lubricants, antistatic agents, light-absorbing dyes, opacifying agents, e.g. titanium oxide and the usual ingredients like hardeners and wetting agents.

The halide composition of the silver halide emulsions used according to the present invention is not specifically limited and may be any composition selected from e.g. silver chloride, silver bromide, silver iodide, silver chlorobromide, silver bromoiodide, and silver chlorobromoiodide. However in the preferred embodiment of roomlight emulsions the silver halide contains preferably at least 70 mole % of chloride.

The photographic silver halide emulsions can be prepared from soluble silver salts and soluble halides according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). The emulsions can be prepared by mixing the halide and silver salt solutions in partially or fully controlled conditions of temperature, concentrations, sequence of addition, and rates of addition. The silver halide can be precipitated according to the single-jet method, the double-jet method, or the conversion method. During precipitation several additives can be present, e.g. dopants containing group VIII elements of the periodic table. The silver halide grains may have a multilayered grain structure. According to a simple embodiment the grains may comprise a core and a shell, which may have different halide compositions. Besides having a differently composed core and shell the silver halide grains may also comprise different phases in between.

The silver halide particles of the photographic emulsions used according to the present invention may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The emulsion can be desalted in the usual ways e.g. by dialysis, by flocculation and re-dispersing, or by ultrafiltration.

Two or more types of silver halide emulsions that have been prepared differently can be mixed for forming a photographic emulsion for use in accordance with the present invention.

The size distribution of the silver halide particles of the photographic emulsions to be used according to the present invention can be homodisperse or heterodisperse. A homodisperse size distribution is obtained when 95% of the grains have a size that does not deviate for more than 30% from the average grain size.

The photographic silver halide emulsions can be used in various types of photographic elements such as e.g. in photographic elements for graphic arts and for so-called amateur and professional photography, diffusion transfer reversal photographic elements, low-speed and high-speed photographic elements and in color photography. In a preferred embodiment of the present invention the emulsions are insensitive negative or direct positive working roomlight emulsions which can be handled under UV poor ambient light. In this case the emulsions contain preferably more than 70 mole % of chloride and show a fine average grain size, e.g. between 0.1 and 0.3 micrometer. In those embodiments of the invention where direct positive emulsions are present the surface of the silver halide grains is preferably prefogged in a conventional way using a reducing agent with or without a gold compound. Useful examples of reducing agents include thioureadioxide, formaldehyde, a polyamine, hydrazine, boron containing compounds, tin(II) chloride and the like. The amount of added fogging agent and the fogging conditions depend on the desired sensitivity level. Fogging can also occur without adding any particular substance but by simply using reducing conditions of pH and pAg.

In those applications where an insensitive direct positive material is concerned the emulsion layer(s) further preferably contain(s) an nitroindazole or nitrobenzimidazole derivative, preferably 5- or 6-nitroindazole or 5- or 6-nitrobenzimidazole. These compounds are very useful in further reducing the minimal density level. These organic desensitizers are preferably present in a concentration ranging from $10^{-4}$ to $10^{-2}$ mole per mole silver halide.

When using negative working light-sensitive silver halide emulsions in the present invention, they can be chemically sensitized or not. In the affirmative case they can be ripened as described e.g. in the above-mentioned "Chimie et Physique Photographique" by P. Glafkides, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB 789,823, amines, hydrazine derivatives, formamidine-sulphinic acids, and silane compounds.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl-pyrrolidone, polyvinyl-imidazole, polyvinyl-pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binder should dispose of an acceptably high number of functional groups, which by reaction with an appropriate hardening agent can provide a sufficiently resistant layer. Such functional groups are especially the amino groups, but also carboxylic groups, hydroxy groups, and active methylene groups.

The gelatin can be lime-treated or acid-treated gelatin. The preparation of such gelatin types has been described in e.g. "The Science and Technology of Gelatin", edited by A. G. Ward and A. Courts, Academic Press 1977, page 295 and next pages. The gelatin can also be an enzyme-treated gelatin as described in Bull. Soc. Sci. Phot. Japan, No. 16, page 30 (1966).

Apart from the spectrally working electron-accepting compounds of the invention and the presence of an organic desensitizer of the nitroindazole or nitrobenzimidazole type, the emulsion layer may comprise other compounds preventing the formation of fog or stabilizing the sensitometric characteristics during storage. Many known compounds can be added as fog-inhibiting agent or stabilizer to the silver halide emulsion. Suitable examples are e.g. benzothiazolium salts, mercaptothiazoles, mercaptobenzothiazoles, mercaptobenzimidazoles, mercaptothiadiazoles, aminotriazoles, benzotriazoles (preferably 5-methyl-benzotriazole), mercaptotetrazoles, in particular 1-phenyl-5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. The fog-inhibiting agents or stabilizers can be added to the silver halide emulsion prior to, during, or after the ripening thereof and mixtures of two or more of these compounds can be used.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic element of the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes e.g. as coating aids, as compounds preventing electric charges, as compounds improving slidability. Preferred surface-active coating agents are compounds containing perfluorinated alkyl groups.

The photographic element of the present invention may further comprise various other additives such as e.g. compounds improving the dimensional stability of the photographic element, UV-absorbers, spacing agents, and plasticizers.

Suitable additives for improving the dimensional stability of the photographic element are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulfoalkyl (meth)acrylates, and styrene sulphonic acids. These compounds can be present in the light sensitive or non-light sensitive layers; in the case of multiple light sensitive layers they can be present in one or more of them.

The support of the photographic material may be opaque or transparent, e.g. a paper support or resin support. When a paper support is used preference is given to one coated at one or both sides with an alpha-olefin polymer, e.g. a polyethylene layer which optionally contains an anti-halation dye or pigment. It is also possible to use an organic resin support e.g. cellulose nitrate film, cellulose acetate film, poly(vinyl acetal) film, polystyrene film, poly(ethylene terephthalate) film, polycarbonate film, polyvinylchloride film or poly-alpha-olefin films such as polyethylene or polypropylene film. The thickness of such organic resin film is preferably comprised between 0.07 and 0.35 mm. These organic resin supports are preferably coated with a subbing layer which can contain water insoluble particles such as silica or titanium dioxide.

The photographic material containing the electron-accepting compounds of the invention can be exposed and processed in any known way adapted to its application purpose and nature of its emulsion. Widely used are the so-called Rapid Access processing systems which employ a superadditive mixture of two developing agents e.g. hydrochinon and 1-phenyl-3-pyrazolidinone or hydrochinon and N-methyl-p-aminophenol. The contain sufficient sulphite ions to provide for stable developer solutions; however these systems do not provide for superior dot quality. Alternatively so-called "hard-dot Rapid Access" processing systems can be used which combine a high sulphite content with a mechanism in which a chemical species is sufficiently active to initiate an infectious development or an infectious development-like high-contrast development. Possible mechanisms can be based on, but are not restricted to hydrazine, hydrochinon or tetrazolium salt chemistries. These systems have the superior quality of classical "lith" systems in addition to the good chemical stability of the conventional Rapid Access systems. An example of such a system is marketed by AGFA under the trade name AGFASTAR.

Preferably the processing occurs in an automatically operated apparatus such as a RAPILINE, marketed by AGFA.

The following examples illustrate the invention without however limiting it thereto.

EXAMPLE 1

General Preparation Method of the Compounds of the Invention

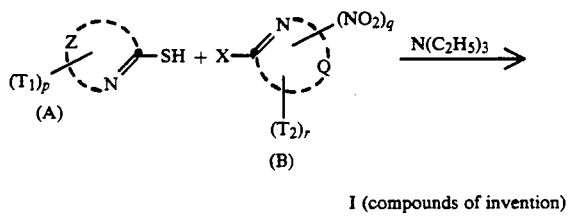

I (compounds of invention)

To a mixture of 0.05 mole heterocyclic mercapto-group containing compound (A) and 0.05 mole triethylamine in 100 ml of dimethylformamide was added whilst stirring at room temperature 0.05 mole heterocyclic halogen containing compound (B), X being Cl or Br. After stirring during four hours the reaction mixture was poured into 500 ml water. The precipitate was filtered off and washed with water. The reaction products were purified by recrystallization or by preparative column chromatography. The chemical structures were confirmed by NMR-analysis. Yield and melting points:

| Compound | I-1; | yield: | 71%; | melting point: | 99° C. |
|---|---|---|---|---|---|
| | I-2 | | 77% | | 76° C. |
| | I-3 | | 80% | | 57° C. |
| | I-4 | | 79% | | 103° C. |
| | I-5 | | 56% | | 46° C. |
| | I-6 | | 71% | | <25° C. |
| | I-7 | | 97% | | 177° C. |
| | I-8 | | 78% | | 223° C. |

EXAMPLE 2

A negative working silver chlorobromide roomlight emulsion consisting of 98 mole % of chloride and 2 mole % of bromide was prepared, showing a cubical crystal structure and a mean grain size of 0.15 micrometer. The emulsion was not chemically sensitized. The emulsion was divided in several aliquot portions and except for one an external electron-accepting compound according to table 1 was added. The portions were coated at 5.0 g/m² of silver halide expressed as $AgNO_3$, with the aid of known additives like a wetting agent, a plasticizer, a filter dye and a hardening agent. The materials were exposed during 6 seconds through a step wedge on the graphic arts exposure unit DL 1000, marketed by AGFA-GEVAERT NV, using a 1000 Watt high pressure metal-halogen lamp. After exposure the materials were processed for 20 seconds at 35° C. in a solution composed of two parts water and one part of the following composition:

| | |
|---|---|
| potassium hydroxide | 93 g |
| potassium metabisulfite | 138 g |
| potassium carbonate | 71 g |
| potassium bromide | 30 |
| methylcellosolve | 60 ml |
| hydrochinon | 60 g |

-continued

| | |
|---|---|
| 1-phenyl-3-pyrazolidinone | 1.45 g |
| 1-phenyl-5-mercaptotetrazole | 90 mg |
| water to make | 1 l |
| pH = 10.85 | |

Following development the materials were fixed in a conventional ammoniumthiosulphate containing fixer, rinsed and dried.

The results of the photographic evaluation are shown in table 1.

TABLE 1

| Compound | Concentration[1] | Fog | Sensitivity[2] | Roomlight Safety[3] |
|---|---|---|---|---|
| — | — | 0.04 | 100 | <10' |
| I-1 | $6.10^{-4}$ | 0.04 | 197 | ±20' |
| I-2 | $6.10^{-4}$ | 0.04 | 156 | >60' |
| I-3 | $6.10^{-4}$ | 0.04 | 165 | >60' |
| I-4 | $5.10^{-4}$ | 0.04 | 214 | >60' |

Notes:
[1] expressed as mole per mole of silver halide;
[2] expressed as relative log Et determined at density 2.00 above fog level; higher number means lower sensitivity and vice versa; without electron-accepting compound the sensitivity has a reference value of 100;
[3] time in minutes during which the fog level rises maximally 0.03 density units during exposure by a 200 lux TL-tube without filter;

Table 1 illustrates the effective desensitizing action of the compounds according to the present invention in negative room light material.

EXAMPLE 3

A direct positive silver chlorobromide roomlight emulsion consisting of 95 mole % of chloride and 5 mole % of bromide was prepared by a double jet precipitation technique, resulting in an average grain size of 0.20 micrometer. During precipitation the emulsion was doped with $Rh^{3+}$ ions using $25.10^{-6}$ mole sodium hexachlororhodate per mole of silver halide. The emulsion was conventionally fogged with $1.0 \times 10^{-4}$ mole of thioureadioxide and $1.25 \times 10^{-6}$ mole of chloroauric acid per mole silver halide. The emulsion was divided in aliquot portions and to each portion 5-nitroindazole (Compound II-1) and/or an electron-accepting compound according to table 2 was added. After coating at 5.0 g of $AgNO_3/m^2$ using conventional coating additives the emulsion layers were exposed during 6 seconds through a step wedge by a 1000 Watt quart-halogen lamp. Then the materials were developed for 20 seconds at 38° C. in a solution of following composition:

| | |
|---|---|
| trisodium phosphate | 60 g |
| sodium sulphite anh. | 60 g |
| hydrochinon | 40 g |
| N-methyl-p-sminofenol sulphate | 2.5 g |
| potassium bromide | 4 g |
| 5-methyl-benzotriazol | 0.3 g |
| 3-diethylamino-1,-propaandiole | 20 g |
| water to make | 1 l |
| pH adjusted to 11.5 | |

Following development the materials were fixed in a conventional ammuniumthiosulphate containing fixer, rinsed and dried.

The results of the photographic evaluation are presented in table 2.

TABLE 2

| Compound | Concentration[1] compound × 10³ | Conc.[1] II-1 × 10³ | Sensitometry Dmin | Dmax | S[2] | Roomlight-safety[3] |
|---|---|---|---|---|---|---|
| — | — | 6.0 | 0.08 | 5.6 | 100 | — |
| I-5 | 4.0 | — | 0.07 | 5.7 | 93 | >20 min |
| I-5 | 4.0 | 3.0 | 0.06 | 5.7 | 92 | " |
| I-6 | 4.0 | — | 0.15 | 5.4 | 100 | " |
| I-6 | 4.0 | 3.0 | 0.06 | 5.7 | 91 | " |
| I-1 | 2.5 | — | 0.05 | 5.6 | 75 | " |
| I-1 | 2.5 | 3.0 | 0.04 | 5.7 | 72 | " |
| I-2 | 2.5 | — | 0.05 | 5.7 | 88 | " |
| I-2 | 2.5 | 3.0 | 0.04 | 5.6 | 83 | " |
| I-4 | 2.2 | — | 0.06 | 5.4 | 98 | " |
| I-4 | 2.2 | 3.0 | 0.05 | 5.5 | 94 | " |

Notes:
[1] expressed as mole per mole of silver halide;
[2] expressed as relative log Et determined at density 0.05 above minimal density; higher value number means higher sensitivity; without electron-accepting compound the sensitivity has a reference value of 100;
[3] time interval during which the maximal density is not diminished below 4.0.

Table 2 illustrates the effective electron-accepting action of the compounds according to the present invention in direct positive roomlight materials. It also shows the reduction of minimal density by combining the products of the invention with 5-nitroindazole.

EXAMPLE 4

A direct positive AgBrI emulsion containing 1% iodide was prepared using a double jet precipitation technique which resulted in a homogeneous emulsion with an average grain size of 0.24 micrometer. After washing and redispersion the emulsion was conventionally fogged using 5 mg of thioureadioxide and $7.5 \times 10^{-6}$ mole of chloroauric acid per mole silver halide. Electron acceptors according to the invention were added (see table 3) to several aliquot portions of the emulsion. After coating at 5.0 g of $AgNO_3/m^2$ using conventional coating additives the emulsion layers were exposed through a step wedge by tungsten light. Then the materials were processed in solutions according to example 2 at the same time and temperature.

The results of the photographic evaluation are presented in table 3.

TABLE 3

| compound (I) | concentration[1] | sensitometry Dmin | sensitivity[2] |
|---|---|---|---|
| — | — | | no reversal |
| R-1 | $2.0 \times 10^{-3}$ | 0.03 | 100 (ref.) |
| I-1 | $9.0 \times 10^{-4}$ | 0.07 | 56 |
| I-2 | $9.0 \times 10^{-4}$ | 0.08 | 54 |
| I-3 | $1.0 \times 10^{-3}$ | 0.08 | 40 |
| I-4 | $8.0 \times 10^{-4}$ | 0.04 | 80 |
| I-6 | $2.5 \times 10^{-3}$ | 0.05 | 76 | notes:
[1] expressed as mole per mole silver halide;
[2] expressed as relative log Et determined at density 0.10 above minimal density; higher number means higher sensitivity; with reference electron-accepting compound R-1 the sensitivity has a reference value of 100.

Table 3 illustrates the effective electron-accepting action and the obtained low minimal density with the compounds of the invention in a direct positive AgBrI emulsion which is handled under classical darkroom conditions.

We claim:

1. Photographic material comprising at least one silver halide roomlight emulsion layer containing at least 70 mole % of chloride and at least one compound represented by the following general formula (I):

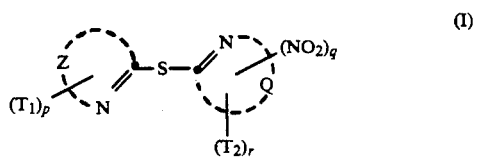

wherein: each of Z and Q which may be the same or different represents the atoms necessary to complete an unsubstituted or substituted nitrogen-containing heterocyclic ring; each of $T_1$ and $T_2$ which may be the same or different represents alkyl, cycloalkyl, alkoxy, aryl, aryloxy, halogen, cyano, hydroxy, carboxyl, sulfo, carbamoyl, acyl, acylamino, sulfamoyl, or sulfonamido; q=1, 2 or 3, and p and r=0, 1 or 2.

2. Photographic material according to claim 1 wherein the nitro containing heterocyclic nucleus is nitropyridine or nitrothiazole.

3. Photographic material according to claim 1 wherein the photographic roomlight emulsion is a negative roomlight emulsion.

4. Photographic material according to claim 1 wherein the photographic roomlight emulsion is a direct positive roomlight emulsion.

5. Photographic material according to claim 4 wherein the emulsion layer containing the direct positive emulsion contains a nitroindazole or nitrobenzimidazole derivative in addition to the compound corresponding to formula (I).

6. Photographic material according to claim 5 wherein the said nitroindazole or nitrobenzimidazole derivative is selected from 5-nitroindazole, 6-nitroindazole, 5-nitrobenzimidazole or 6-nitrobenzimidazole.

7. Photographic material according to claim 1 wherein the compound according to formula (I) is present in a concentration ranging from $10^{-5}$ mole to $10^{-1}$ mole per mole of silver halide.

8. Photographic material according to any of claim 5 or 6 wherein the said nitroindazole or nitrobenzimidazole derivative is present in a concentration ranging from $10^{-4}$ to $10^{-2}$ mole per mole of silver halide.

* * * * *